United States Patent
Chalekian et al.

(10) Patent No.: US 9,592,099 B2
(45) Date of Patent: Mar. 14, 2017

(54) TRANSAPICAL COLLAPSIBLE VALVE REFERENCE FIXTURE

(71) Applicant: St. Jude Medical, Cardiology Division, Inc., St. Paul, MN (US)

(72) Inventors: Aaron J. Chalekian, Savage, MN (US); James Leo Kurk, New Richmond, WI (US); Yousef F. Alkhatib, Edina, MN (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 677 days.

(21) Appl. No.: 13/669,924

(22) Filed: Nov. 6, 2012

(65) Prior Publication Data

US 2013/0123911 A1    May 16, 2013

Related U.S. Application Data

(60) Provisional application No. 61/559,933, filed on Nov. 15, 2011.

(51) Int. Cl.
    *A61B 19/00*    (2006.01)
    *A61B 17/00*    (2006.01)

(52) U.S. Cl.
    CPC .............. *A61B 90/50* (2016.02); *A61B 90/39* (2016.02); *A61B 2017/00243* (2013.01); *A61B 2090/571* (2016.02)

(58) Field of Classification Search
    CPC ....... A61F 2/958; A61B 19/201; A61B 90/39; A61B 2090/571; A61B 2017/00243; A61B 90/50
    See application file for complete search history.

(56) References Cited

U.S. PATENT DOCUMENTS

| | | | |
|---|---|---|---|
| 2008/0086150 A1* | 4/2008 | Mathis et al. | 606/130 |
| 2009/0171370 A1* | 7/2009 | Yoon | A61F 2/4609 606/130 |
| 2009/0216247 A1* | 8/2009 | Collette | A61B 17/155 606/130 |
| 2011/0060339 A1* | 3/2011 | de Wekker | 606/80 |

* cited by examiner

*Primary Examiner* — Richard Louis
(74) *Attorney, Agent, or Firm* — Lerner, David, Littenberg, Krumholz & Mentlik, LLP (57) ABSTRACT

A device for positioning a reference element during aortic valve implantation surgery. The device includes a first extension member having a proximal end and a distal end, a connection member adapted to connect the first extension member to a support, and a coupling having a first end connected to the connection member and a second end connected to the proximal end of the first extension member so that the first extension member is moveable in multiple planes relative to the support. At least one reference datum is operatively connected to the distal end of the first extension member and extends in a straight line, the reference datum being moveable between a first position and a second position to enable precise locating of the reference datum during the aortic valve implantation surgery.

14 Claims, 6 Drawing Sheets

TRANSAPICAL COLLAPSIBLE VALVE REFERENCE FIXTURE

CROSS-REFERENCE TO RELATED APPLICATIONS

This application claims the benefit of the filing date of U.S. Provisional Application No. 61/559,933, filed Nov. 15, 2011, the disclosure of which is hereby incorporated by reference herein.

BACKGROUND OF THE INVENTION

Heart valve disease, and particularly aortic heart valve disease, has been a medical problem for many years. Over time, natural aortic valves may leak, causing aortic insufficiency or regurgitation, or may become blocked or exhibit limited function due to aortic stenosis. Early heart disease treatments included insertion of either a mechanical or prosthetic valve through a median sternotomy and open heart surgery.

Although improvements to open heart surgery have been made over the years, resulting in a significant lessening of mortality and morbidity rates, open heart surgery still remains a very involved and complicated undertaking. Moreover, post-operative recovery is often lengthy. Efforts therefore continue to develop non-surgical techniques for managing heart valve disease.

One such non-surgical technique involves percutaneous aortic valve replacement. With this technique, a valve is transported to the heart via, for example, the femoral vein through a small incision made in the groin. However, no matter how successful, this technique also exhibits limitations. For example, the path from the groin to the aortic valve via the femoral vein is relatively lengthy and requires crossing of the mitral valve. Crossing of the mitral valve can itself induce mitral insufficiency and reduced cardiac output.

More recently, surgeons have been opting for a transapical approach to aortic valve replacement. Under this approach, surgeons reach the native aortic valve with a catheter preloaded with a replacement valve. Generally, the catheter and valve assembly are placed through the apex of the heart in an antegrade approach. With this technique, precise and exact positioning of the replacement valve is required. Heretofore, surgeons manipulated the catheter delivery device exclusively by hand. However, it would be advantageous to assist with the process by providing both stability for the catheter delivery device and a reference datum for the surgeon. It would also be beneficial to provide novel surgical methods for taking advantage of such a fixed reference mechanism.

BRIEF SUMMARY OF THE INVENTION

The present invention addresses these and other needs. In accordance with an embodiment of the invention, a device for positioning a reference element during aortic valve implantation surgery may include a first extension member having a proximal end and a distal end; a connection member adapted to connect the first extension member to a support; a first coupling having a first end connected to the connection member and a second end connected to the proximal end of the first extension member so that the first extension member is moveable in multiple planes relative to the support; and at least one reference datum operatively connected to the distal end of the first extension member and extending in a straight line, the reference datum being moveable between a first position and a second position to enable precise locating of the at least one reference datum during the aortic valve implantation surgery. The support may be selected from the group consisting of surgical tables and surgical retractors.

The at least one reference datum may be a rigid rod. The at least one reference datum may also include a first rigid rod extending in a first direction, a second rigid rod extending in a second direction orthogonal to the first direction, and a third rigid rod extending in a third direction orthogonal to the first and second directions.

The first coupling may have a first portion fixedly connected to the connection member and a second portion fixedly connected to the proximal end of the first extension member. The first coupling may include a moveable joint interposed between the first portion and the second portion. The moveable joint may be a ball and socket joint.

The positioning device may further include a reference block having first and second attachment mechanisms, the first attachment mechanism including an elongated bore for connecting the reference block to a rigid rod, and the second attachment mechanism being adapted to connect an aortic valve delivery catheter to the reference block.

The positioning device may further include a second extension member having a proximal end and a distal end; and a second coupling having a first end connected to the distal end of the first extension member and a second end connected to the proximal end of the second extension member.

Additionally, the positioning device may include a reference element operatively connected between the distal end of the first extension member and the at least one reference datum.

BRIEF DESCRIPTION OF THE DRAWINGS

The subject matter regarded as the invention is particularly pointed out and distinctly claimed in the concluding portion of the specification. The invention, however, both as to organization and method of operation, together with the features, objects, and advantages thereof, may best be understood by reference to the following detailed description when read with the accompanying drawings in which:

DETAILED DESCRIPTION

Preferred embodiments of the transapical collapsible valve reference fixture are disclosed below in accordance with the present invention. Where like elements have been depicted in multiple embodiments, like reference numerals have been used in the multiple embodiments for ease of understanding.

In this description, the terms "reference fixture" and "transapical collapsible valve reference fixture" are utilized interchangeably to refer to the transapical collapsible valve reference fixture of the present invention. The terms "proximal" and "distal" are to be taken as relative to the point at which the reference fixture of the present invention is attached or mounted to a fixed support, such as a table. "Proximal" is to be understood as relatively close to the fixed support when traveling along the length of the reference fixture, and "distal" is to be understood as relatively further away from the fixed support when traveling along the length of the reference fixture.

Figure 1:
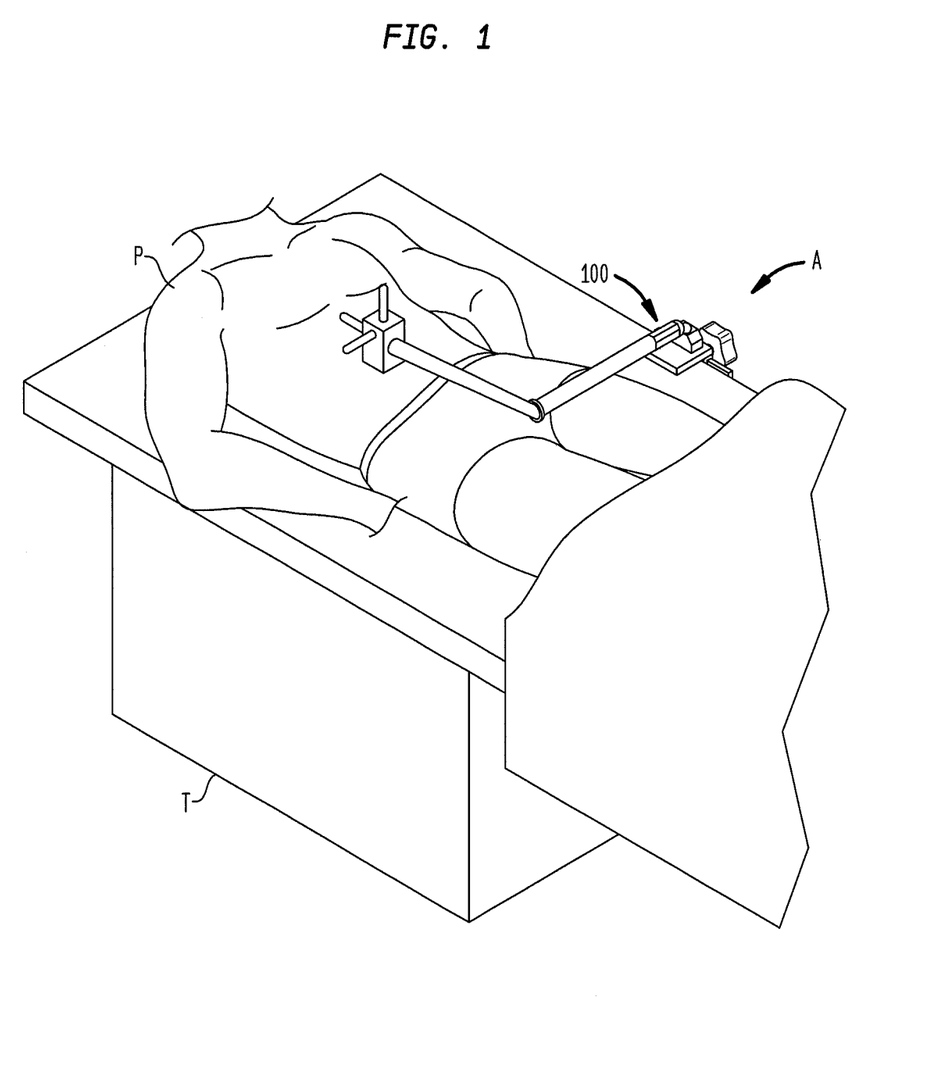
FIG. 1 is a diagrammatic view of a surgical arena, including a representative view of a reference fixture in accordance with certain aspects of the present invention.

Referring to FIG. 1, there is depicted a diagrammatical view of a surgical arena A. Within the arena A are a surgical table T and a patient P laying on the table. Attached to the table T is a reference fixture 100 in accordance with one embodiment of the present invention. As shown in FIG. 1, and as will be discussed in more detail below, the reference fixture 100 is attached to the table T at one end of the fixture. The reference fixture 100 extends outwardly from its connection with the table T and is positionable over the patient P, such as when the patient is undergoing transapical heart valve replacement. In other embodiments, the reference fixture may be attached to retractors used during the surgical procedure, or to other fixed points in the surgical arena A, rather than to the table T. As also will be discussed, the reference fixture 100 extends over the patient P to create a fixed reference point for the user (e.g., a surgeon or an interventional cardiologist) during the surgical procedure.

Figure 2:
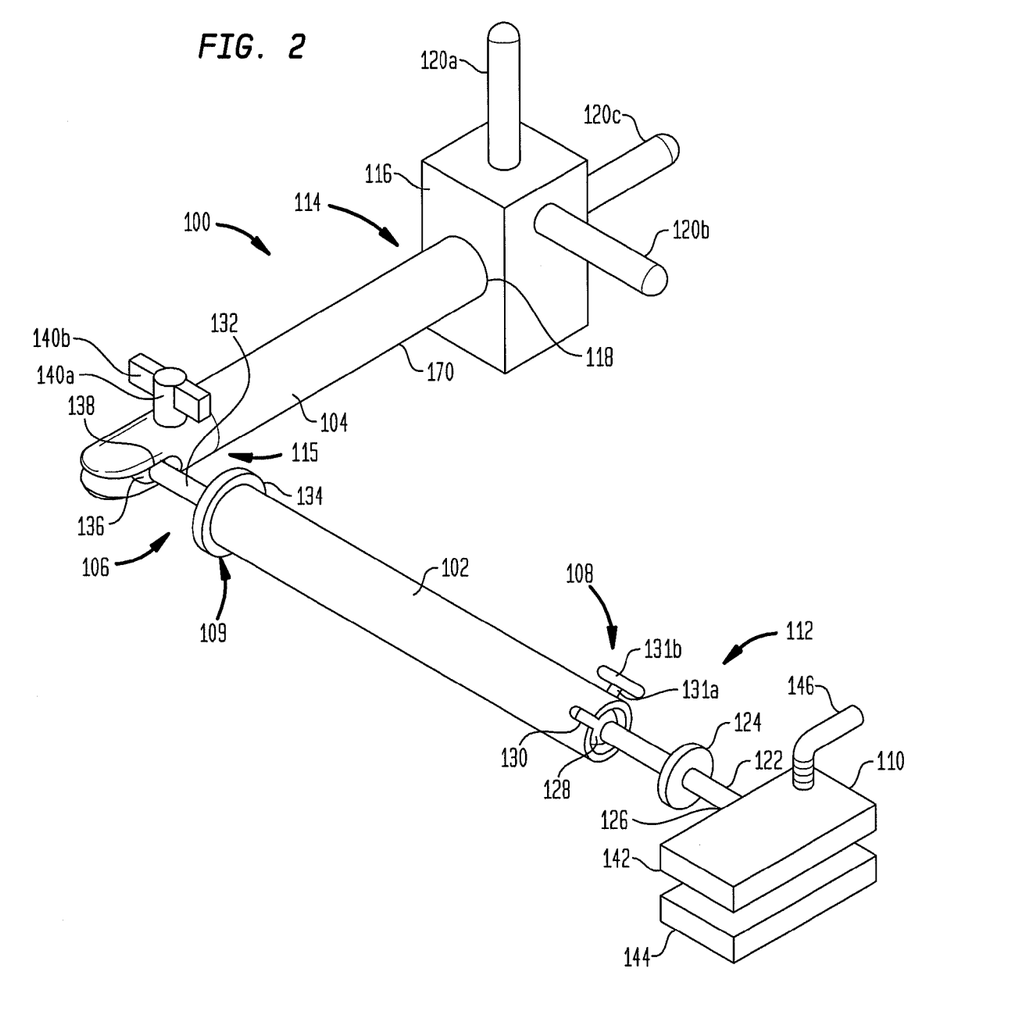
FIG. 2 is a perspective view of a representative reference fixture in accordance with certain aspects of the present invention.

FIG. 2 is a more detailed, perspective view of the representative reference fixture 100 in accordance with certain aspects of the present invention. The reference fixture may include a number of arms, such as first arm 102 and second arm 104. Reference fixture 100 may have only a single arm, or may have more than two arms as desired. However, two arms are typically sufficient to provide structural stability while still permitting adequate movement and positioning about the surgical arena A. In this embodiment of FIG. 2, arms 102 and 104 are joined together by a joint 106 to enable relative movement between the two arms. At the proximal end 108 of arm 102 (and the proximal end of reference fixture 100) is a connection member for connecting reference fixture 100 to a fixed support, such as table T. As used herein, the term "fixed support" does not necessarily mean that the support is immovable. Rather, the term "fixed support" is intended to reflect the fact that the support is stable, and will not move unintentionally during the use of reference fixture 100. Thus, while table T may be moveable when desired, it may be locked in place so as to not move during a valve replacement procedure. The connection member may be a standard two plate clamp 110 having a first plate 142 and a second opposed plate 144 that may be brought together or moved apart by a threaded lever 146. Clamp 110 may be attached to arm 102 by a joint 112.

Rather than clamp 110, fixation device 100 may utilize any other mechanism for secure attachment to a fixed support. For example, the proximal end 108 of arm 102 may be positioned within an appropriately sized aperture in the support and held in place therein by a tight frictional fit, or by a set screw. Alternatively, the proximal end 108 of arm 102 may fit through an aperture in the fixed support and may be held therein by a pin, nut, spring loaded arms, clamping member, or other securing mechanism. Still further, the proximal end 108 of arm 102 may be configured with a "quick clamp" to slidingly engage a side rail of a surgical table, as will be described more fully below.

A datum block 116 may be connected to the distal end 114 of arm 104 (and the distal end of reference fixture 100). The datum block 116 may be a generally rectangular body with three reference datum 120a, 120b, 120c extending therefrom, preferably in mutually orthogonal directions. Thus, reference datum 120a may extend from one face of datum block 116 in a direction substantially orthogonal to arm 104; reference datum 120b may extend from another face of reference block 116 in a direction substantially orthogonal to both arm 104 and reference datum 120a; and reference datum 120c may extend from yet another face of datum block 116 in a direction substantially parallel with arm 104 and orthogonal to both reference datum 120a and reference datum 120b. Moreover, each pair of reference datum 120a, 120b and 120c may be coplanar, with the third reference datum being substantially orthogonal to the plane defined by the other two. In a variant hereof, reference datum 120a, 120b, 120c may extend directly from arm 104 without the use of a datum block. Each of reference datum 120a, 120b and 120c may be in the form of a straight rod projecting outwardly from the rectangular body.

Reference fixture 100 may include more than three reference datum or less than three reference datum as needed. As few as one reference datum may be adequate. However, three reference datum provide a preferred number of reference lines giving the user a sufficient number of positioning options without unduly interfering in the surgical arena A.

As stated above, arm 104 may be connected to arm 102 by a joint 106, and arm 102 may be connected to clamp 110 by a joint 112. Joints 106 and 112 are intended to provide a maximum amount of maneuverability between the connected elements, and therefore each may be in the form of a ball and socket joint.

Joint 112 may include a post 122 that is threaded at one end 126 for connecting the post to another object; in the case of joint 112, to clamp 110. A knurled knob 124 at an intermediate position on post 122 may help to rotate the post relative to the clamp. Rather than a threaded connection, it is contemplated that post 122 may be securely joined to clamp 110 in other ways generally known in the art. At its opposite end, post 122 includes a ball 128. The ball 128 represents the "ball" of ball and socket joint 112.

The "socket" portion of ball and socket joint 112 is provided at the proximal end 108 of arm 102. In this regard, the proximal end 108 of arm 102 may be hollow, and may have a somewhat spherical internal shape adapted to complement the shape of ball 128. Alternatively, the proximal end 108 of arm 102 may be provided with an insert having a somewhat spherical internal shape for mating with the shape of ball 128. Where arm 102 includes an insert, the insert may be made from a polymer that reduces the friction and wear resulting from the movement of ball 128 relative to arm 102.

The proximal end 108 of arm 102 may also be provided with one or more slits or slots 130 extending in the length direction of the arm a short distance from the arm's free end. Slits or slots 130 split the proximal end 108 of arm 102 and any insert therein into segments that can flex radially outward so that ball 128 may be inserted into the split socket, and may freely rotate therein. The rotation of the ball 128 within the socket at the proximal end 108 of arm 102 enables the arm to be positioned at virtually any desired angle in three-dimensional space. A threaded rod 131a having a knob 131b on one end thereof may extend through an aperture in a segment of arm 102 on one side of slot 130 (and through the corresponding segment of the polymer insert where present) and threadedly engage a threaded aperture on a segment of arm 102 on the opposite side of slot 130. By turning threaded rod 131a in a tightening direction, the segments of arm 102 on opposite sides of slot 130 (and the corresponding segments of the polymer insert where present) may be drawn closer to one another so that slot 130 narrows and the split socket tightly engages ball 128. The frictional engagement between ball 128 and the segments of arm 102 on opposite sides of slot 130 (or between ball 128 and the segments of the polymer insert on opposite sides of slot 130) prevents the ball from rotating relative to the socket, thereby locking arm 102 in a fixed position relative to clamp 110.

Joint 106 has a similar structure to joint 112. Thus, joint 106 includes a post 132 that is threaded on one end for connection to the distal end 109 of arm 102. A knurled knob 134 at an intermediate position on post 132 may help to tighten the threaded engagement. The opposite end of post 132 includes a ball 136 that is receivable in a "socket" provided at the proximal end 115 of arm 104. As with joint 112, the socket may be formed by the internal shape of the hollow proximal end 115 of arm 104, or by a polymer insert provided in the hollow proximal end of the arm. One or more slits or slots 138 extending in the length direction of arm 104 from the free proximal end 115 thereof define segments in the proximal end of the arm (and in any insert therein) that can flex radially outward so that ball 136 may be inserted into the split socket and may rotate freely therein. The rotation of the ball 136 within the socket at the proximal end 115 of arm 104 enables the arm to be positioned at virtually any desired angle in three-dimensional space relative to arm 102. A threaded rod 140a having a knob 140b at one end thereof may extend through an aperture in a segment of arm 104 on one side of slot 138 (and through the corresponding segment of the polymer insert where present) and threadedly engage a threaded aperture on a segment of arm 104 on the opposite side of slot 138. Turning threaded rod 140a in a tightening direction may draw the segments of arm 104 on opposite sides of slot 138 (and the corresponding segments of the polymer insert where present) closer to one another so that slot 138 narrows and ball 136 is unable to rotate relative to the socket, locking arm 104 in a fixed position relative to arm 102. Where reference fixture 100 includes one or more additional arms, such arms may be connected in series with arms 102 and 104 using similar "ball and socket" type joints. It will be appreciated that joints 106 and 112, and any similar joints in reference fixture 100, may be formed as other types of joints in lieu of "ball and socket" joints, such as hinge joints, screw joints, planar joints and the like.

While the ends of arms 102 and 104 have been described as forming the socket portion of the ball and socket joint, additional elements may be provided for this purpose. This may be particularly useful in reference fixtures in which the arms 102 and 104 are formed from materials which do not readily flex to receive the ball portion of the joint. Such materials may include, for example, lightweight plastic or carbon fiber. Where such materials are used for arms 102 and 104, a companion structure, preferably of metal, may attach to each arm 102, 104, such as by threaded engagement, welding, adhesive, force fit, or other types of connection. Such companion structure may include the slits or slots 130, 138 and the through aperture and threaded aperture on opposite sides of the slits or slots for receiving threaded rods 131, 140.

By providing two ball and socket joints, the reference fixture 100 of FIG. 2 provides a great degree of adjustment for the user. This is true even though the connection between arm 104 and datum block 116 is shown as a simple threaded connection 118. Rather than a threaded connection, datum block 116 could be connected to arm 104 by a rotatable post joint to enable datum block 116 to rotate about the central longitudinal axis of arm 104. Such connection could also be a ball and socket joint similar to joints 106 and 112, or another type of joint, such as an elbow joint, hinge joint, etc.

Figure 3:
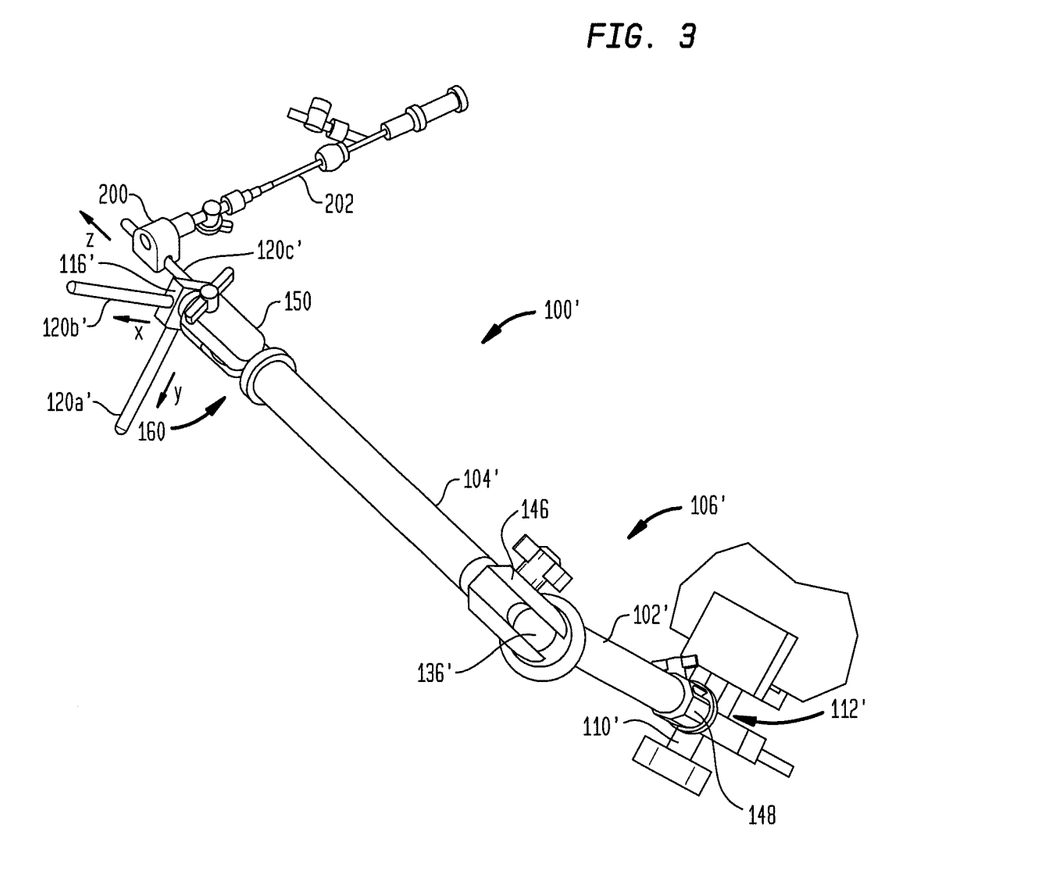
FIG. 3 is a perspective view of another reference fixture in accordance with certain aspects of the present invention.

A reference fixture 100' utilizing a ball and socket joint in place of the threaded connection 118 is shown in FIG. 3. Thus, reference fixture 100' includes three ball and socket joints, a first joint 160 between datum block 116' and arm 104', a second joint 106' between arms 102' and 104', and a third joint 112' between arm 102' and clamp 110'. Similar to ball and socket joints 106 and 112 described above, each of joints 160, 106' and 112' includes a ball attached to the end of one member that fits within a split socket on the end of an adjacent member, wherein the connection between the ball and socket may be fixed by tightening a threaded fastener.

It will be appreciated that the sockets in reference fixture 100' are provided by socket connectors 146, 148 and 150, which connect the end of one member to the ball at the end of a next adjacent member. For example, referring to FIG. 3, socket connector 146 may be fixedly connected to the proximal end of arm 104', and may provide a split socket for connecting to the ball 136' at the distal end of arm 102'. In addition, socket connector 150 may be fixedly connected to datum block 116', and may provide a split socket for connecting to the ball at the distal end of arm 104'.

Datum block 116' includes reference datum 120a', 120b', and 120c' extending therefrom. As previously described, it is preferred that these reference datum extend in mutually orthogonal directions, as depicted by the x, y and z axes in FIG. 3. Datum 120b' extends along the x axis; datum 120a' extends along the y axis in a direction that is orthogonal to the x axis and coplanar therewith; and datum 120c' extends along the z axis in a direction that is orthogonal to both the x axis and the y axis. Datum block 116' may include additional reference datum, and/or reference datum 120a', 120b' and 120c' may extend in different directions than those shown, all depending on the needs of the user.

Figure 4:
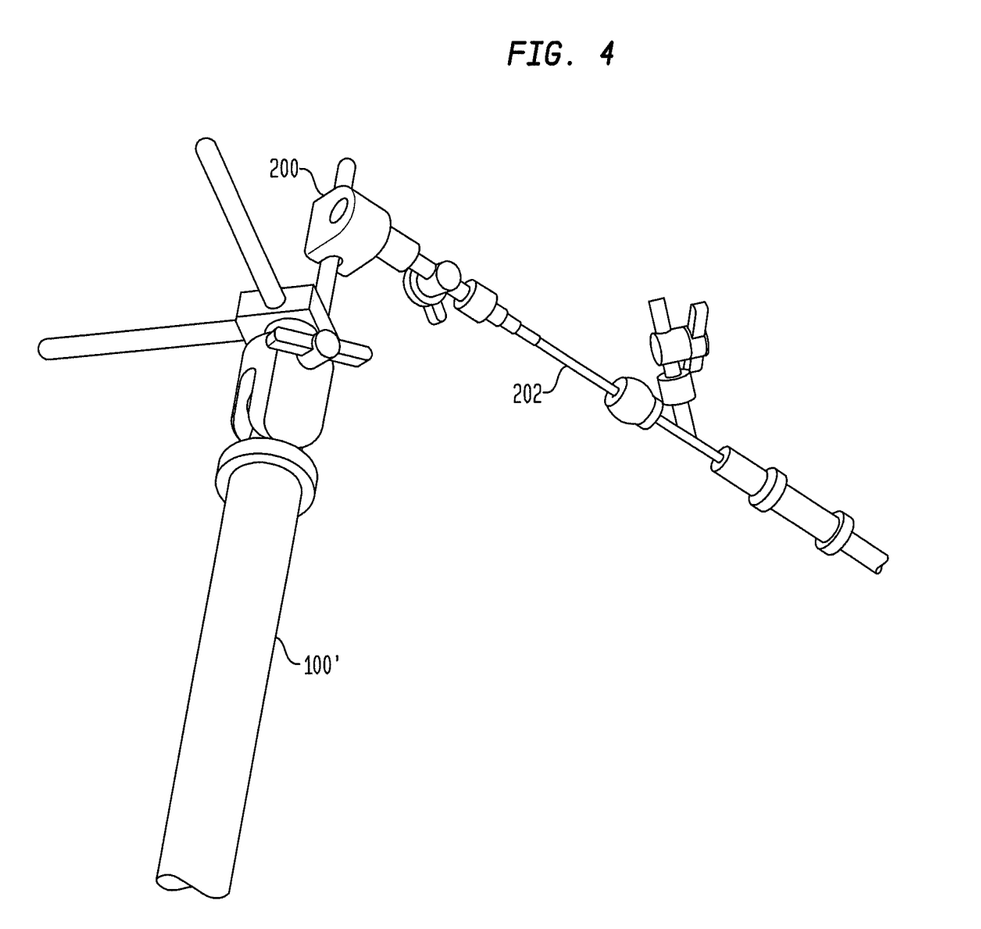
FIG. 4 is an enlarged perspective view of a portion of the reference fixture shown in FIG. 3.

Referring again to FIG. 3, mounted to reference datum 120c' is a reference block 200, the details of which will be described below. Reference block 200 enables catheter based valve delivery system 202 to be mounted to reference fixture 100'. A more detailed view of the connection of valve delivery system 202 to reference fixture 100' is shown in FIG. 4.

Figure 5:
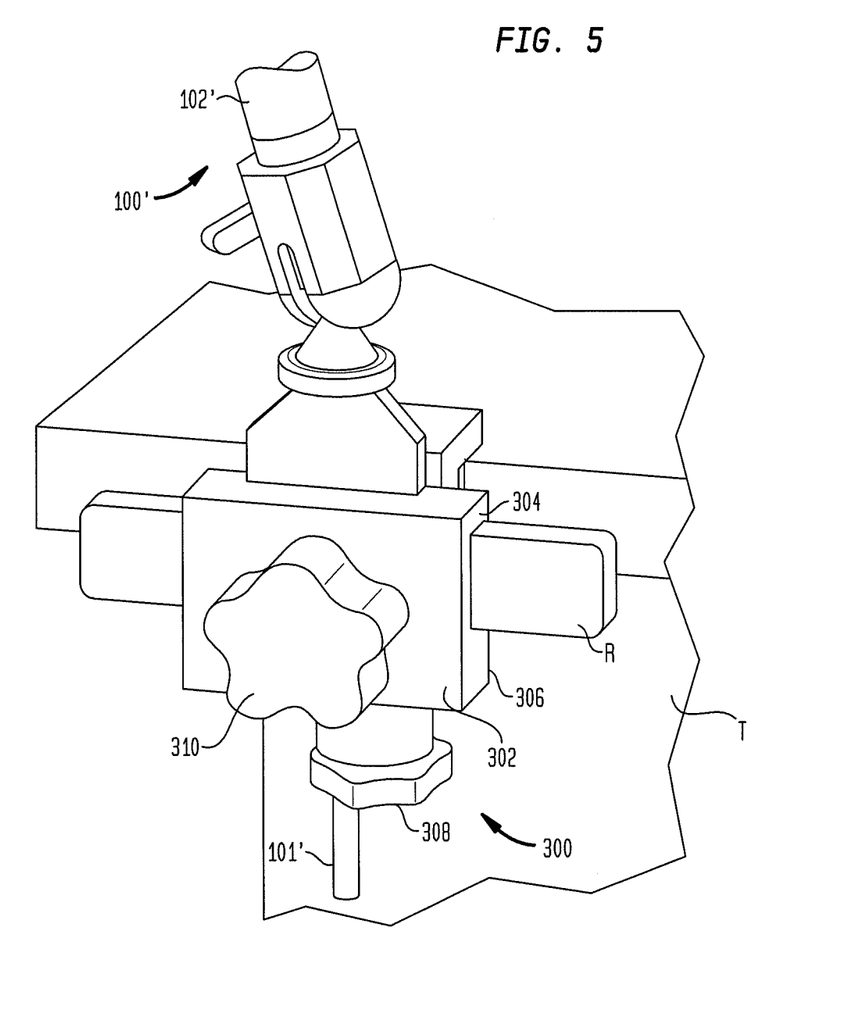
FIG. 5 is an enlarged perspective view of another portion of the reference fixture shown in FIG. 3.

As noted above, the reference fixtures of the present invention may be connected to the rail of a surgical table so as to be slidable therealong. FIG. 5 is a perspective view of a clamp 300 for making such connection. Clamp 300 may be connected to the side rail R of the table T using quick mount rail techniques well known to one of ordinary skill in the art. In that regard, clamp 300 may include a body, the main portion 302 of which confronts the front surface of rail R. A first jaw 304, integrally formed with the main portion 302, extends over the top of rail R and into engagement with the back surface of the rail. A second jaw 306, formed separately from the main portion 302, extends below the bottom of rail R and into engagement with the back surface of the rail. A threaded rod (not shown) may join jaw 306 to jaw 304, and a knob 308 at the end of the threaded rod may be used to rotate the threaded rod so as to bring jaw 306 closer to jaw 304, thereby tightening clamp 300 against the top and bottom surfaces of rail R. A second threaded rod (not shown), threadedly engaged through the main portion 302 of the clamp body, may be rotated by a knob 310 at one end thereof to fix a post 101' at the proximal end of reference fixture 100' to clamp 300. With reference fixture 100' fixed to clamp 300, knob 308 may be turned to loosen jaws 304 and 306 from rail R. Clamp 300 may then be slid in either direction along rail R until reference fixture 100' is in a desired position, at which point knob 308 may be turned in an opposite direction to tighten jaws 304 and 306 and fix the clamp to the rail.

Figure 6:
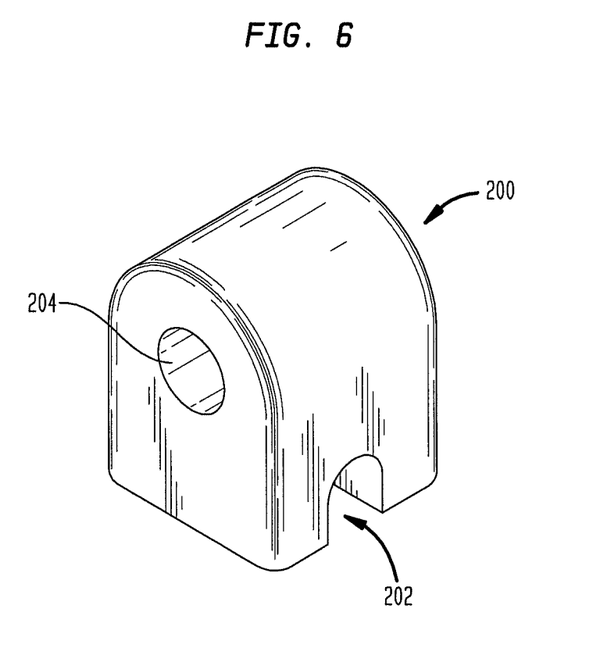
FIG. 6 is a perspective view of a reference block in accordance with certain aspects of the present invention.

FIG. 6 is a perspective view showing the details of the reference block 200 referred to above. Reference block 200 includes a reference datum slot 202 sized and configured to slidingly engage any one of reference datum 120a-c, 120a'-c'. The sliding engagement should be sufficiently loose that reference block 200 may be slid onto and along reference datum 120a-c, 120a'-c', but also sufficiently tight that the reference block will be fixed on the reference datum in a relatively tight relation when the pushing or pulling force is terminated. Reference block 200 also includes an arrangement appropriate for affixing a catheter delivery system thereto. One such arrangement is an aperture 204 extending through reference block 200 in a direction orthogonal to reference datum slot 202. Aperture 204 may be sized to receive a luer fitting on the proximal end of the catheter delivery system. Although shown as a rounded body, the shape of reference block 200 is not critical, and may be square, rectangular, or any other geometric or non-geometric shape as desired or dictated by the procedure being performed and the apparatus with which the reference fixture is being used. Preferably, reference block 200 and all parts of the reference fixtures described herein are configured from a lightweight plastic or metal that may be sterilized and reused.

The reference fixtures of the present invention enable a user to precisely position a catheter delivery system, particularly for a prosthetic cardiac valve, for improved surgical performance. Such reference fixtures may be positionable using only a single hand, and are particularly useful in a transapical valve replacement approach. In this regard, certain catheter delivery systems include sheaths that may move relative to one another and relative to the catheter in general. With the present invention, a fixed sheath may be connected to reference block 200, for example through a female luer fitting, and aligned precisely for valve delivery into the patient. A moveable sheath may thereafter be maneuvered to deploy the prosthetic valve while the reference block and fixed sheath are held in a fixed position relative to the patient.

In order to use reference fixture 100 or 100' in a surgical procedure, the reference fixture is first attached to the operating table or to another fixed support, such as chest retractors, using clamp 110, clamp 300 or other suitable clamp. The delivery catheter may then be connected to reference block 200 and the user may position the delivery catheter in an appropriate position and orientation vis-à-vis the native anatomy of the patient. After fine tuning the position and orientation, and making any necessary adjustments, the user may fix the members of the reference fixture relative to one another by turning knobs 131b and 140b to tighten joints 112 and 106, respectively, and performing a similar procedure to tighten any other joints of the reference fixture. The user may then perform the valve replacement procedure using the fixed reference to hold the catheter's position during deployment of the prosthetic valve.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

It will be appreciated that the various dependent claims and the features set forth therein can be combined in different ways than presented in the initial claims. It will also be appreciated that the features described in connection with individual embodiments may be shared with others of the described embodiments.

The invention claimed is:

1. A positioning device for use during aortic valve implantation surgery, the device comprising:
    a first extension member having a proximal end and a distal end;
    a connection member adapted to connect the first extension member to a fixed support;
    a first coupling having a first portion connected to the connection member and a second portion connected to the proximal end of the first extension member so that the first extension member is moveable in multiple planes relative to the support;
    at least one reference datum operatively connected to the distal end of the first extension member and extending in a straight line, the reference datum including a rigid rod moveable between a first position and a second position to enable precise locating of the reference datum during the aortic valve implantation surgery;
    a reference block slidably mounted to the rigid rod and securable at a fixed position along the rigid rod so that the reference block is distal to the distal end of the first extension member and at a spaced distance from the first extension member, the reference block having an attachment mechanism adapted to connect an aortic valve delivery catheter to the reference block;
    a reference element operatively connecting the distal end of the first extension member to the at least one reference datum; and
    a second coupling interposed between the distal end of the first extension member and the reference element and enabling the reference element to move in multiple planes relative to the first extension member.

2. The positioning device of claim 1, wherein the support is selected from the group consisting of surgical tables and surgical retractors.

3. The positioning device of claim 1, wherein the at least one reference datum includes a first rigid rod extending in a first direction, a second rigid rod extending in a second direction orthogonal to the first direction, and a third rigid rod extending in a third direction orthogonal to the first and second directions.

4. The positioning device of claim 1, further comprising
    a second extension member having a proximal end and a distal end; and
    a third coupling having a first portion connected to the distal end of the first extension member and a second portion connected to the proximal end of the second extension member.

5. The positioning device of claim 4, wherein the second coupling has a first portion connected to the distal end of the second extension member and a second portion connected to the reference element.

6. The positioning device of claim 5, further comprising a moveable joint interposed between the first portion and the second portion of each of the first coupling, the second coupling and the third coupling.

7. The positioning device of claim 6, wherein each of the moveable joints is a ball and socket joint.

8. The positioning device of claim 7, wherein each of the ball and socket joints includes a split socket.

9. The positioning device of claim 1, wherein the first coupling includes a moveable joint interposed between the first portion and the second portion.

10. The positioning device of claim 9, wherein the moveable joint is a ball and socket joint.

11. The positioning device of claim 10, wherein the ball and socket joint includes a split socket.

12. The positioning device of claim 1, wherein the reference block is securable at a spaced distance along the rigid rod from the reference element.

13. A positioning device for use during aortic valve implantation surgery, the device comprising:
   an extension member extending in an elongation direction between a proximal end and a distal end;
   a connection member adapted to connect the extension member to a fixed support;
   a first coupling having a first end connected to the connection member and a second end connected to the proximal end of the extension member so that the extension member is moveable in multiple planes relative to the support;
   at least one reference datum operatively connected to the distal end of the extension member and extending in a straight line, the reference datum including a rigid rod moveable relative to the extension member between a first position in which the straight line is at a first angle to the elongation direction and a second position in which the straight line is at a second angle to the elongation direction different from the first angle to enable precise locating of the reference datum during the aortic valve implantation surgery;
   a reference block slidably mounted to the rigid rod and securable at a fixed position along the rigid rod so that the reference block is distal to the distal end of the extension member and at a spaced distance from the extension member, the reference block having an attachment mechanism adapted to connect an aortic valve delivery catheter to the reference block;
   a reference element operatively connecting the distal end of the extension member to the at least one reference datum; and
   a second coupling interposed between the distal end of the extension member and the reference element and enabling the reference element to move in multiple planes relative to the extension member.

14. The positioning device of claim 13, wherein the reference block is securable at a spaced distance along the rigid rod from the reference element.

* * * * *